US007137864B2

(12) United States Patent
Swanson

(10) Patent No.: US 7,137,864 B2
(45) Date of Patent: Nov. 21, 2006

(54) METHODS AND REAGENTS FOR TREATING HONEYBEES FOR PARASITIC MITES

(76) Inventor: Melvin J. Swanson, 5290 Mt. Carmel Rd., Carver, MN (US) 55315

( * ) Notice: Subject to any disclaimer, the term of this patent is extended or adjusted under 35 U.S.C. 154(b) by 59 days.

(21) Appl. No.: 10/889,399

(22) Filed: Jul. 12, 2004

(65) Prior Publication Data

US 2006/0009122 A1    Jan. 12, 2006

(51) Int. Cl.
  *A01K 51/00*    (2006.01)
(52) U.S. Cl. ......................................................... 449/2
(58) Field of Classification Search .................... 449/2; 514/557, 770; 424/405, 484, 486, 487
  See application file for complete search history.

(56) References Cited

U.S. PATENT DOCUMENTS

| | | | |
|---|---|---|---|
| 4,581,042 A | 4/1986 | Willmore | 51/293 |
| 4,927,813 A | 5/1990 | Bernstein | 514/65 |
| 5,645,845 A | 7/1997 | Neumann et al. | 424/405 |
| 6,037,374 A | 3/2000 | Kochansky et al. | 514/557 |
| 6,475,061 B1 | 11/2002 | Huang | 449/12 |
| 6,620,025 B1 | 9/2003 | Scheuneman et al. | 449/2 |
| 6,646,014 B1 | 11/2003 | Watkins | 514/731 |

FOREIGN PATENT DOCUMENTS

| | | | |
|---|---|---|---|
| CA | 2237484 | | 11/1998 |
| EP | 1402900 | * | 6/2001 |
| RU | 2 222 189 | | 1/2004 |
| RU | 2 225 104 | | 3/2004 |
| WO | WO 97/47193 | | 12/1997 |

OTHER PUBLICATIONS 1 pg. "Anti-Mite Gel Gets Commericial License," Science Update, p. 23, Agricultural Research/Nov. 1998.
7 pgs. "A comparison between the efficiency of summer treatments using formic acid and Taktic® against *Varroa jacobsoni* in beehives," Lupo et al., Apidologie 1990, vol. 21, pp. 261-267.
4 pgs. "The Control of Parasitic Bee Mites: *Varroa jacobsoni, Acarapis woodi* and Tropilaelaps clareae with Formic Acid," Hoppe et al., Apicultural Research, American Bee Journal, Nov. 1989, vol. 129, pp. 739-742.
4 pgs. "Development of a Gel Formulation of Formic Acid for Control of Parasitic Mites of Honey Bees," Kochansky et al., Journal of Agricultural Food Chemistry, 1999, vol. 47, pp. 3850-3853.
11 pgs. "Effective Fall Treatment of *Varroa jacobsoni* (Acari: Varroidae) with a New Formulation of Formic Acid in Colonies of Apis mellifera (Hymenoptera: Apidae) in the Northeastern United States," Calderone, Journal of Economic Entomology 2000, vol. 93, No. 4, pp. 1065-1075.
3 pgs. "Effects of Formic Acid Treatment on Infestation of Tracheal Mites, *Acarapis woodi* (Rennie), in the Honey Bee, *Apis mellifera* L," Liu et al., Apicultural Research, American Bee Journal 1992, vol. 132, pp. 666-668.
5 pgs. "Efficacy of formic acid in gel for *Varroa* control in *Apis mellifera* L.: importance of the dispenser position inside the hive," Eguaras et al., Veterinary Parasitology 2003, vol. 111, pp. 241-245.
Abstract 1pg. "Formic acid application methods for the control of honey bee tracheal mites," Nelson, et al., Bee-Science 1994 vol. 3(3), pp. 128-134.
3 pgs. "Initial Results of the Field Treatment of Honey Bee Colonies Infested with *Varroa jacobsoni* Using Formic Acid in Hot Climates," Bracey et al., Apicultural Research, American Bee Journal, Nov. 1989, vol. 129, pp. 735-737.
12 pgs. (In German) "Labor- Und Feldversuche Mit Der Illertisser Milbenplatte Als Neue Anwendungsform Der Ameisensaure Im Rahmen Der Varroatose-Bekampfung," Wachendorfer et al., Apidologie, 1985, vol. 16, No. 16, pp. 291-306.
Abstract 1 pg. "New Methods for the Treatment of varroa disease. Formic Acid—laboratory and field tests," Ritter, et al., Allgemeine-Deutsche-Imkerzeitung 1980, vol. 14, No. 5, pp. 151-153.
4 pgs. "A New Product with Formic Acid for *Varroa jacobsnoni* Oud., Control in Argentina. I. Efficiacy," Eguaras et al., Journal of Veterinary Medicine 2001, vol. 48, pp. 11-14.
Abstract 1 pg. "Results with the treatment of varroa disease in Tunisia," Ritter et al., Allgemeine-Deutsche-Imkerzeitung 1980, vol. 14, No. 5, pp. 150-151.
4 pgs. "Short-Interval Treatments with Formic Acid for Control of *Varroa jacobsnoni* in Honey Bee (*Apis mellifera*) Colonies in Cold Climates," Fries, Swedish Journal of Agriculture Res. 1989, 19, pp. 213-216.
4 pgs. PCT International Search Report filed Jul. 7, 2005.

* cited by examiner

*Primary Examiner*—Teri Pham Luu
*Assistant Examiner*—Elizabeth Shaw
(74) *Attorney, Agent, or Firm*—Kagan Binder, PLLC

(57) ABSTRACT

The invention provides controlled release compositions for treatment of parasitic mites in honeybees, the compositions composed of a covalently crosslinked polymer gel and an active agent that includes a salt of formic acid. The invention also provides methods for controlling parasitic mites in honeybees, the methods involving treating the honeybees with a controlled release composition composed a covalently crosslinked polymer gel and an active agent that includes a salt of formic acid. The invention further provides a kit for treatment of parasitic mites in honeybees, the kit including an envelope that contains a controlled release composition of the invention. Optionally, the active agent can include formic acid.

33 Claims, No Drawings

METHODS AND REAGENTS FOR TREATING HONEYBEES FOR PARASITIC MITES

FIELD OF THE INVENTION

The invention relates to compositions and methods for controlling infestations of honeybee colonies. More particularly, the invention relates to compositions and methods for treating honeybees for parasitic infestations, such as mite infestations.

BACKGROUND OF THE INVENTION

Parasitic mites have caused serious problems both for the beekeeping industry and more broadly in agriculture, since honeybees are important for pollination of many important crops. There are two types of parasitic mites that cause problems for honeybees. Both *Varroa jacobsoni* and the tracheal mite *Acarapis woodi* cause infestations that have resulted in extensive reductions in honeybee populations. The successful management of honeybees in the face of these pests requires multiple approaches for control, including breeding of resistant strains and various treatments and control measures.

Various treatments have been attempted to control parasitic mites in honeybees, although limitations of currently available treatments include toxicity of the chemicals used, marginal effectiveness, inconvenience of use, difficulties in registration of the composition with environmental agencies, mite resistance, and/or contamination of beeswax. There are currently two products registered in the United States for control of *Varroa*: Apistan®. (Wellmark International, Dallas, Tex.), a plastic strip containing fluvalinate, and Check-Mite+™ (Bayer), a plastic strip containing coumaphos. In addition, another product, called Api Life Var, containing thymol, is available in a few states. This product is stated to be only 75% effective, so does not provide a complete treatment. Unfortunately, there are now strains of mites that are resistant to both fluvalinate and coumaphos. Furthermore, there are concerns about contamination of honey and beeswax with these agents.

Other treatments have been used on an experimental basis with varying results. Essential oils have been used with mixed success. Experimental work has been carried out with an ester of formic acid, methylformate. Results of that work are unknown at the present time. Tracheal mites can sometimes be controlled with menthol or, less effectively, by use of vegetable oil patties placed in the hive. However, none of these materials is active against both types of parasitic mites.

Formic acid has been used quite effectively in much of the world to control mite infestation, but it is not currently registered for use in the United States. Formic acid vapors are known to be effective for controlling parasitic mites in honeybees. However, formic acid is corrosive and toxic; thus, using it can be hazardous for the user. Methods and compositions for application of formic acid have taken a variety of forms, including liquid, support materials soaked in liquid formic acid, strips of formic acid, and menthol-paste.

Formic acid has been used in liquid form in Europe and Canada and has been shown to control parasitic mites of honeybees in a wide variety of situations. The first comprehensive report on such use of formic acid appeared in a special issue on varroatosis (Ritter and Ruttner. 1980. Allg. Dtsch. Imkerztg. vol. 14, pp. 151–153). Subsequently, the "Illertisser Mite plate" (IMP), a cardboard-like material that could be soaked with formic acid and placed in the hive was developed (Wachendorfer et al. 1985. Apidologie. vol. 16, pp. 291–306). This method, or modifications of it, was tested against parasitic bee mites in a number of countries, including Germany (Hoppe et al. 1989. Amer. Bee J. vol 129, pp. 739–742), Sweden (Fries, I. 1989. Swedish J. Agric. Res. vol. 19, pp. 213–216) and Dubai (Bracey and Fisher. 1989. Amer. Bee J. vol. 129, pp. 735–737). Other known application methods have included soaked cheesecloth (Liu and Nasr. 1992. Amer. Bee J. vol. 132, pp. 666–668) and containers with wicks (Sharma et al. 1983. Indian Bee J. vol. 45, pp. 1–2; Lupo and Gerling. 1990. Apidologie. vol. 21, pp. 261–267). Nelson et al. (1994. Bee Science. vol. 3, no. 3, pp. 128–134) disclosed formic acid application for controlling tracheal mites and compared treatments using liquid formic acid, formic acid gel-strips, menthol-paste and the German product IMP.

Most of the above-mentioned methods use varying concentrations of dilute liquid formic acid, and most require multiple applications. In addition, use of the IMP apparatus often necessitates the removal of part of the honeycomb from the hive to meet space requirements.

Another approach that has been developed for dispensing formic acid involves mixing either polyacrylic acid or fumed silica with a formic acid solution to make a gel. This approach is described in U.S. Pat. No. 6,037,374 and in J Agric Food Chem 47(9): 3850–3 (1999). This technology was also developed into a commercial product that was registered for use in the United States under the trade name Apicure™ (BetterBee). However, due to problems of leakage from the packaging, it was removed from the market after a short time.

There have been numerous reports indicating the effectiveness of formic acid in gel for controlling parasitic mites in honeybees (Vet Parasitol 111(2–3):241–5 (2003) and J Vet Med B 48(1):11–4 (2001). Formic acid is very corrosive and safely dispensing it inside the beehive has been problematic. Moreover, because formic acid is a strong acid, it can destroy gelling agents and/or prevent adequate gel stability (thus resulting in failure to form a stable gel, leakiness of the resulting gel, and other similar stability problems). Formic acid can be difficult to mix with other reagents as well, which can also contribute to instability problems of resulting gels. Further, current methods can require handling liquid formic acid, frequent applications and/or extensive hive manipulation.

In addition to the above concerns, there is increasing resistance by *Varroa* to the currently approved products. If additional effective treatments were available, this could provide the ability to alternate treatment courses, thus minimizing the occurrence of such resistance.

SUMMARY OF THE INVENTION

The invention relates generally to compositions and methods for treating honeybees for infestations. The invention can provide one or more advantages when used to treat honeybees for infestations, particularly mite infestations. In preferred embodiments, the invention provides a controlled release composition for treatment of parasitic mites in honeybees, the composition comprising a covalently crosslinked polymer gel and an active agent comprising a salt of formic acid. In some embodiments, the active agent can comprise free formic acid, or a combination of a salt of formic acid and formic acid.

In another aspect, the invention provides methods for controlling parasitic mites in honeybees, the methods comprising treating the honeybees with a controlled release composition comprising a covalently crosslinked polymer gel and an active agent comprising a salt of formic acid. In some embodiments, the active agent can comprise free formic acid, or a combination of a salt of formic acid and formic acid.

In yet another aspect, the invention provides a packaged product for treating honeybees for infestations. According to these aspects, the invention provides a controlled release composition for treatment of parasitic mites in honeybees in a stable packaging.

In one preferred embodiment, the inventive compositions and methods provide less hazardous and more convenient techniques for treating honeybees, as well as greater control of the rate of release of the active agent. In preferred embodiments, the rate of release of the active agent is at least partly controlled by the polymer gel composition itself. This is in contrast to prior methods and compositions that rely upon packaging of a pest control composition to control release of the active agent. In preferred embodiments, the invention allows the option of formulating gels having different release rates for use under different conditions of weather and hive conditions, such as levels of mite infestation.

In another aspect of the invention, the active agent is incorporated into a covalently crosslinked polymer gel. The resulting gel can be cast into any desirable shape, for example, by polymerizing appropriate monomers in a solution containing the active ingredient and optional additives. According to this aspect of the invention, the active ingredient is provided in a mechanically stable, firm, and/or non-flowing state. This is in contrast to prior compositions that are provided in the form of a paste-like gel that is capable of flowing (and are thus more hazardous for the user and for shipping and handling). Moreover, the covalently crosslinked polymer gel formulation of the invention can, in preferred embodiments, allow greater control over rates of release of the active agent compared with liquid formic acid. Preferably, the inventive covalently crosslinked polymeric gel compositions do not require manipulation by the user to change physical or chemical characteristics of the composition, such as dilution of the composition prior to application to a hive (as can be required when liquid formic acid is used).

In preferred aspects, the covalently crosslinked polymer gel also provides an advantageously stable polymeric matrix for delivery of the active agent. When a polymer gel is formulated to include a high concentration of ionic species, the stability of the polymer gel can be difficult to maintain. More specifically, the polymer gels of the invention include high concentrations of ionic species (acid ions). The covalent crosslinking creates a polymeric matrix that maintains the acid ions in a stable, non-flowable format. The inventive polymer gels provide a more stable matrix than gels that are formed using ionic associations or ionic crosslinking. The framework of the polymer gel that is formed by ionic associations or crosslinking may be susceptible to attack by ionic species (for example, acid ions) causing a breakdown of the polymer gel (which, in turn, can result in a flowable gel). In preferred aspects, the components of the inventive compositions are easily combined to provide a well-dispersed mixture containing active agent that can be subsequently polymerized to provide a stable polymer gel. In other words, the active agent can be dissolved in the other components of the polymer gel, and the mixture can be polymerized to form a uniform distribution of active agent within the polymer gel. In preferred aspects, the resulting covalently crosslinked polymer gel provides a mechanically stable product that does not readily flow and/or release liquid formic acid.

In other preferred aspects, the invention can provide polymeric materials wherein stability of the polymeric material is independent of any packaging considerations and/or characteristics. For example, the mechanically stable polymer gel provides a matrix that releases formic acid vapors only, and not liquid formic acid. As such, the packaging materials and conditions for the inventive compositions can be much more flexible than prior formulations that rely upon liquid formic acid or formic acid compositions that are flowable.

According to one preferred embodiment of the invention, the active agent can include a salt of formic acid, either as the sole active agent, or in combination with formic acid. According to these embodiments, the active ingredient can be provided in a partially neutralized form that can advantageously reduce hazards associated with handling the composition.

These and other aspects and advantages will now be described in more detail.

DETAILED DESCRIPTION

The embodiments of the present invention described below are not intended to be exhaustive or to limit the invention to the precise forms disclosed in the following detailed description. Rather, the embodiments are chosen and described so that others skilled in the art can appreciate and understand the principles and practices of the present invention.

The inventive compositions and methods provide controlled release of vapors from an active agent contained within a covalently crosslinked polymer gel for treatment of honeybees. The controlled release compositions are formulated to behave in a desired manner under defined conditions, characterized by a controlled administration of vapors from the active agent over a given time frame in comparison to raw active material. The inventive formulations described herein are capable of maintaining a desired vapor concentration of formic acid in the atmosphere of a defined volume of a bee environment, such as a beehive. The controlled release composition is capable of releasing a regulated dose of vapors from the active agent at a desired rate, preferably releasing a defined quantity of formic acid vapors into a beehive over a chosen period of time, such as the reproductive cycle of the targeted honeybee population. Preferably, controlled delivery of the vapors from the active agent is accomplished over a period of about 2–3 weeks, as this period constitutes at least one honeybee brood cycle.

The controlled release thus provides a desired concentration of formic acid vapors within the bee environment by including an effective amount of the active agent in the polymeric gel. The effective amount of the active agent is the amount an active agent alone, or together with other substances (as described herein), that produces the desired effect (such as reduction in mite population) in a bee colony. During treatment, such amounts can depend upon such factors as the size of the beehive (in terms of bee population as well as physical volume), the particular pest targeted by the inventive methods and formulations, environmental conditions (such as temperature, humidity and the like), infestation level, and like factors within the knowledge and expertise of a bee keeper. Preferably, the effective amount of the active agent provides a sufficient concentration of formic acid vapors to achieve at least 70%, or at least 75%, or at least 80% infestation control of the parasite without effecting significant mortality of the honeybee population. One preferred vapor concentration for controlling mites is in the range of about 0.08 to about 0.16 mg/L (or about 40–80 ppm), (Exp Appl Acarol. 2003;29(3–4):303–13.) One of skill in the art, given the present description, can readily determine the effective amount of the active agent required to treat a honeybee population for mite infestation.

The inventive compositions and methods can be applied over a treatment course. The treatment course refers to the dosage rate of one or more active agents over time, to provide a desired concentration of formic acid vapors to a bee population. Thus, factors of a treatment course include dosage rate and time course of treatment (total time during which the active agent(s) is administered). The inventive methods provide formic acid vapors that can penetrate the brood cells or comb (and thereby reach pests affecting bee larvae in the brood). In preferred embodiments, the time course of treatment is in the range of about 2 to about 3 weeks (although treatment for periods longer than 3 weeks is certainly possible as well).

The present invention is directed to methods and apparatuses for effectively controlling parasitic mites in honeybees, and in particular for delivering active agents to a bee population in a controllable manner. Such methods and compositions in accordance with the present invention can advantageously be used to provide flexibility in treatment duration and conditions. In particular, the present invention has been developed for controllably providing one or more active agents to a bee population for a desired treatment course. For purposes of clarity, the present description often refers to the administration of a single active agent for treatment of mite infestations. However, it is understood that the inventive composition and methods can include more than one active agent, for example, when a combination of formic acid and a salt of formic acid is used.

In one aspect, the invention provides controlled release compositions for treatment of parasitic mites in honeybees, the composition comprising a covalently crosslinked polymer gel and an active agent comprising a salt of formic acid. In some embodiments, the active agent can comprise free formic acid, or a combination of a salt of formic acid and formic acid.

The active agent is transported from the controlled release polymer gel composition via the vapor phase onto the target pest. In a preferred aspect of the invention, the active agent evaporates or sublimates from the controlled release polymer gel in a regulated concentration into the atmosphere of the bee environment (such as a bee hive) and maintains a preselected concentration range for at least a 2 week treatment course, or a 2–3 week treatment course.

In one preferred embodiment, effective control of infestations, particularly *varroa* infestations, can be achieved such that the infestation is reduced to a level of 30% or less, or 25% or less, or 20% or less of a starting infestation level, wherein the starting infestation level is the infestation level prior to treatment initiation. Preferably, the reduction in infestation levels to 20% is accomplished within a typical honeybee brood cycle, for example, the 2–3 week brood cycle of honeybees.

The invention provides controlled release of an active agent from a covalently crosslinked polymer gel. In some preferred embodiments, the covalently crosslinked polymer gel can be formed by polymerization of acidic monomers. In preferred embodiments, the acidic monomers are selected to have a pKa similar to or lower than formic acid (lower than 3.75 at 20° C.), such as, for example, acrylic acid, maleic acid, or 2-acrylamido-2-methyl-1-propanesulfonic acid (AMPS). Mixtures of monomers can also be used, including comonomers such as methacrylic acid, maleic acid (or maleic anhydride), acrylamide and N,N-dimethylacrylamide, N,N-dimethylacrylic acid, hydroxyethylmethacrylate, hydroxyethylacrylate. In preferred embodiments, polymerization can be initiated by free radical generators such as ammonium persulfate or 4,4'-azobis(4-cyanovaleric acid).

The amount of monomers used to form the polymer gel is not critical, so long as the desired consistency (for example, mechanical stability, firmness) of the resulting polymer gel is achieved.

According to the invention, the polymer gel can be crosslinked using bifunctional monomers, such as for example N,N-methylene-bis-acrylamide (BIS), N,N'-(1,2-dihydroxyethylene)bisacrylamide, 3-(acryloyloxy)-2-hydroxypropyl methacrylate, ethylene glycol dimethacrylate, or ethylene glycol diacrylate.

In one embodiment, the inventive methods comprise the application of a single active agent. According to this embodiment, a salt of formic acid can be incorporated into the crosslinked polymer gel and formic acid released therefrom.

In some preferred embodiments, the methods entail application of a combination of free formic acid and a salt of formic acid. Exemplary salts of formic acid include, without limitation, sodium formate, potassium formate, lithium formate, ammonium formate, and tetramethylammonium formate. A preferred salt is sodium formate.

In still further embodiments, the methods entail application of free formic acid as the active agent. Preferably, the covalently crosslinked polymer gel provides an improved stable delivery vehicle for the formic acid.

Preferably, when the covalently crosslinked polymer gel includes a salt of formic acid, one or more releasing agents is also included with the polymer gel composition. In preferred embodiments, the releasing agent is a nonvolatile acid that acts to release formic acid from the salt. Exemplary nonvolatile acids that can be used according to these embodiments include malic acid, oxalic acid, citric acid, lactic acid, phosphoric acid, and sulfuric acid. However, it will be understood that a releasing agent need not be added as a separate component to the polymer gel composition, particularly in situations when other components of the polymer gel composition can provide the function of assisting release of the formic acid from the salt. For example, when nonvolatile acids are utilized as monomers in the polymeric gel (such as acrylic acid, methacrylic acid, maleic acid), these acids can function to assist release of the formic acid from the salt. According to these embodiments, an additional releasing agent need not be provided.

The concentration of the releasing agent is not particularly critical to the invention, but the releasing agent is preferably present in excess of the concentration of formic acid salt. In some embodiments, for example, the releasing agent is present in an amount of 2-fold molar excess relative to the concentration of the formic acid salt.

The active agent is present in the covalently crosslinked polymer gel in an amount sufficient to provide a desired vapor concentration of formic acid within the bee environment. In some embodiments, the formic acid is present in an amount up to about 70% by weight of the crosslinked polymer gel, or up to about 65% by weight, or in the range of about 1% to about 70%, or about 10% to about 60%. In some embodiments, the salt of formic acid is present in an amount up to about 50% by weight of the crosslinked polymer gel, or in the range of about 1% to about 50%, or about 10% to about 40% (all percentages by weight, based upon the total weight of the crosslinked polymer gel composition). When the active agent comprises a combination of free formic acid and salt of formic acid, the free formic acid can be present in an amount up to about 70% by weight, or up to about 65% by weight, or in the range of about 1% to about 70%, or about 10% to about 60%, and the formic acid salt can be present in an amount up to about 50% by weight of the crosslinked polymer gel, or in the range of about 1% to about 50%, or about 10% to about 40%.

Optionally, the invention further includes an acceptable support material associated with the crosslinked polymer gel. The support material can be fabricated of any material that does not significantly negatively impact the bee population to be treated. Preferably, the support material does not adversely affect the release of active agent from the polymer gel composition. For example, suitable support material can include fibrous material, such as paper-based materials, or polymeric-based materials (for example, high density polyethylene fibrous materials such as Tyvek™ (DuPont)), or other nonwovens. Exemplary support materials can provide such characteristics as durability, permeability, absorbance, and lightweight.

The support material can be associated with the polymer gel to form a polymer gel product. The resulting polymer gel product can be held together in any suitable manner, for example, utilizing suitable fixtures such as adhesive, binders (such as fibers, cords, threads, and the like), staples, and the like. When included, the support material can provide a gel composition that is more easily handled by the user. The inventive polymer gels are preferably sufficiently firm and mechanically stable, such that they can be used without any further physical or chemical manipulation by the end user (for example, diluting, drying, or the like).

Although not required for use of the invention, the crosslinked polymer gel can be used in combination with various types of dispensing systems that allow emission of formic acid vapor. Perforated containers can be useful, whether pre-perforated with some mechanism for uncovering the perforations or perforated by various means just prior to use. Alternatively, a shallow plastic tray dispenser can be utilized. Any type of dispensing system can be utilized according to the invention. The dispensers can be placed in several locations within the bee environment such that the vapors are distributed in the bee hive.

In a typical preparation of a controlled release composition, appropriate monomers are polymerized in a solution containing the selected active agent (salt of formic acid, or a combination of free formic acid and a salt of formic acid) and a crosslinking agent. Optionally, a polymerization initiator and/or catalyst are also present in the solution. In the presence of free radicals, a chain reaction is initiated in which monomers are polymerized into long chains. When a crosslinking agent is included in the polymerization reaction, the chains become crosslinked to form a gel, whose porosity is determined by the length of the chains and the degree of crosslinking. The crosslinking of the monomers gives the obtained polymer gel a mechanically stable matrix structure.

More specifically, polymerization can be accomplished by dissolving the monomers, crosslinkers, and active agent in solvent (such as distilled water). An polymerization initiator, such as an initiator peroxide (for example, ammonium persulfate) can be added to the solution. Optionally, polymerization catalysts, such as a quaternary amine (for example, N,N,N',N'-tetramethylenediamine, TEMED) can be added to the solution as well. The reagents are thoroughly mixed and allowed to stand until the crosslinked polymer gel is formed (the desired gel firmness is achieved). When it is desired to provide the gel in a cast form, the solution can be poured into a casting container before significant polymerization has taken place. Preferably, an inert gas (such as nitrogen, argon, helium, and the like) is provided to the polymerizing mixture, since atmospheric oxygen is a free radical scavenger that can inhibit polymerization. Once the polymer gel is obtained, it can be removed from the casting container (if used), and prepared for ultimate use. Such preparative steps can include, for example, cutting the polymer gel to a desired size, providing a support material on one or more surfaces of the polymer gel, and/or packaging the polymer gel in a suitable package until use. For example, if the polymer gel is not intended to be used immediately, it can be desirable to package the polymer gel in a sealed container until use.

In preferred aspects, the invention provides means of dispensing formic acid vapors without the need to handle liquid formic acid, which is caustic and toxic, and thus is hazardous to work with. As opposed to previously developed methods for making a formic acid gel by dissolving or suspending a gelling agent in a formic acid solution, the invention forms a covalently crosslinked polymer gel by polymerizing appropriate monomers in a solution containing a salt of formic acid, or some combination of free acid and a salt of formic acid, as well as crosslinking agents, to form a crosslinked gel. One advantage of this invention is that the gel containing active agent does not flow or leak liquid from the gel. In preferred embodiments, the gel is also sufficiently strong to make it easy to handle without exposure to liquid formic acid.

According to some preferred aspects of the invention, the rate and duration of release of formic acid vapors can be adjusted to obtain optimal control of the release of formic acid vapor. For example, the extent of crosslinking of the gel can affect the release of formic acid vapor from the gel, as described herein. The strength and concentration of the nonvolatile acid can also affect the rate and duration of release of formic acid vapors, for example, by releasing the formic acid from its salt form.

One exemplary embodiment of the invention is a gel slab of approximately 12 cm×12 cm by approximately 5 mm thick. The gel slab can be overlaid on each side with a fibrous or absorbent material, such as pieces of Tyvek™ or paper towel, cut to the appropriate size for ease of handling and to prevent the gel from sticking to the packaging or other surfaces. Optionally, the fibrous material can extend beyond the gel or be configured to enclose the gel (as in an envelope), to allow handling without contacting the gel. For use, the gel slabs can simply be removed from packaging and placed into a bee environment (such as a hive). Desirably, one gel slab can be placed in the top of the hive and another gel slab placed in the bottom of the hive, either onto the bottom board through the entrance, or under a bottom screen as part of an integrated pest management system. See Vet Parasitol 2003 Feb. 13;111(2–3):241–5.

Once the polymer gel compositions are formed according to the methods described herein, the compositions can be suitably processed and packaged for use by a consumer. In preferred embodiments, the polymer gel compositions are shelf stable. As used herein, "shelf stable" refers to the compositions of the invention being suitable for storage at ambient temperatures (such as room temperature) without the polymer gel composition substantially breaking down by, for example, hydrolysis of linkages forming the polymeric matrix and the like, and becoming unsuitable for use to treat honeybees. In preferred embodiments, the compositions are stable for a period of several months, or six months or more, or a year or more.

In one preferred aspect of the invention, the stability of the inventive compositions is independent of the type of packaging utilized in connection with the compositions. The inventive covalently crosslinked polymer gels provide a mechanically stable gel that retains the active agent (formic acid salt and/or formic acid) and thus reduces the risk of release of liquid formic acid. Therefore, the inventive compositions can be packaged in any material that is stable when exposed to formic acid vapors.

In some embodiments, it can be desirable (but not required) to provide stable packaging for the product. Preferably, such stable packaging can be formed from materials that are resistant to degradation by acid (acid-stable), including, but not limited to, such metallic materials as foil, and/or polymeric materials such as polyolefin materials. It can be desirable to minimize or prevent the release of formic acid vapors from the product. In part, this can be accomplished by virtue of the stability of the gel itself—the covalently crosslinked polymer gel maintains the active agent within the polymeric gel and allows release of the formic acid vapors. Optionally, to reduce the possibility of formic acid vapor release during storage, a gas-impermeable packaging can be utilized with the product. According to these particular embodiments, the packaging can be heat-sealed or can comprise a container that is suitably sealed such that gas is not able to escape the packaging. Suitable packaging can include pouches, bags, box containers, and the like.

Optionally, the controlled release composition is placed within an envelope of material. The envelope is configured to encase the composition and permit release of acid vapors during use of the article. Thus, the envelope is provided as a component of the article to be used by the end user (such as a bee keeper). Use of an envelope to enclose the material can provide several advantages, such as allowing the user to handle the article without contacting the polymeric gel material and/or the acid components of the article. Further, the envelope can provide a convenient format for use of the controlled release product, since the product can be easily handled, placed within the hive environment, and moved (if necessary) during use of the product.

When used, the envelope can be fabricated from any suitable material that is vapor-permeable yet impermeable to polar liquids. Exemplary materials for the envelope include hydrophobic porous materials that are woven or nonwoven. The hydrophobic material can be fibrous material provided in the form of fabric, sheets, or the like. Exemplary nonwoven materials are polyolefins, such as polypropylene, polyethylene, and the like. One preferred nonwoven polyolefin is a high-density polyethylene material (such as commercially available from DuPont™ under the product name Tyvek™).

The envelope can be utilized as the sole packaging of the polymer gel material or can be used in combination with another form of packaging. In one embodiment of a combination-packaging format, the envelope is provided as an inner packaging of the final controlled release product. According to these particular embodiments, the final controlled release product includes a combination packaging composed of the inner envelope (that encloses the polymer gel) and an outer packaging (that encloses the envelope-containing polymer gel). The controlled release polymer composition is provided within the envelope, which is in turn provided within an outer packaging as described above. This type of combination packaging can be advantageous in several aspects. The combination packaging can allow the end user to select the number of enveloped compositions to utilize at a time, while leaving the remaining enveloped compositions in the outer packaging for later use. Further, such combination packaging provides a format that is safely handled by the end user, since exposure to liquid acid components is minimized. Still further, such combination packaging can enhance the self-life of the products.

According to the invention, the envelope can be used as a replacement for, or in addition to, a support material associated with the polymer gel. Support materials are described elsewhere herein.

The following examples illustrate the present invention without, however, limiting the same thereto.

EXAMPLE 1

Synthesis of a Gel Containing Formic Acid and a Salt of Formic Acid

Sodium formate (18 gm, 265 mmole) and methylene-bis-acrylamide (BIS) (300 mg) were dissolved in 40 ml (1.06 mole) of formic acid and 20 ml of distilled water. To this solution was added 25 ml (365 mmole) of acrylic acid, 100 μl of N,N,N',N'-tetramethylethylenediamine (TEMED) and 1.2 gm of ammonium persulfate. The final volume of the solution prior to polymerization was 91 ml. The solution was poured into a 10 cm×10 cm plastic box. Nitrogen was bubbled through the solution, then the box covered tightly and put into an oven at about 50° C. overnight to polymerize into a gel. The gel was removed from the box and overlaid on each side with pieces of paper towel cut to approximately the size of the gel and stored in a sealed container until used.

EXAMPLE 2

Testing of Formic Acid/Sodium Formate Gels in Active Beehives

Two gel slabs prepared by the procedure of Example 1 were placed in a beehive, consisting of three hive bodies, one at the top under an inner cover and one under a screen at the bottom of the hive. The formic acid vapor concentration was measured by inserting a tube into a hole drilled in the bottom hive body using a Draeger tube (Fisher, Cat. No. 17-985-234) and an Accuro Draeger pump Fisher, Cat. No. 17-986-70A) following the manufacturer's instructions. After 24 hours, the concentration was 23 ppm. The temperature was 68° F. After seven days, the concentration was 40 ppm. The temperature was 70° F. After 11 days, the concentration was 12 ppm when the temperature was 52° F. Two other hives were treated similarly with similar results.

EXAMPLE 3

Synthesis of a Gel Containing Formic Acid and Sodium Formate in Crosslinked Polyacrylic Acid for Laboratory Comparison Methylene-bis-acrylamide (25 mg) was dissolved in 4.0 ml of formic acid. To that solution was added 2.0 ml of acrylic acid (29.2 mmole). In a separate solution, 1.0 gm of sodium formate and 125 mg of ammonium persulfate were dissolved in 1.0 ml of distilled water. The solutions were combined to achieve a final volume of 8.5 ml. The combined solution was poured into a plastic box. Nitrogen was bubbled through the solution, then the box covered tightly and put into an oven at about 50° C.–60° C. overnight to polymerize into a gel. After overnight in the oven, the gel was removed and covered on each side with paper towel pieces cut to approximately the dimensions of the gel and stored in a zip lock plastic bag until used.

EXAMPLE 4

Synthesis of a Gel Containing Formic Acid and Sodium Formate in Crosslinked Poly(acrylic/maleic Acid) for Laboratory Comparisons Maleic anhydride (2.0 gm, 20.4 mmole) and methylene-bis-acrylamide (25 mg) were dissolved in 3.0 ml of formic acid (79.5 mmole). To that solution was added 1.8 ml of acrylic acid (26.25 mmole). In a separate solution, 1.8 gm (26.5 mmole) of sodium formate and 125 mg of ammonium persulfate were dissolved in 2.0 ml of distilled water. The solutions were combined to achieve a final volume of 9.0 ml. The combined solution was poured into a plastic box. Nitrogen was bubbled through the solution, then the box covered tightly and put into an oven at about 50° C.–60° C. overnight to polymerize into a gel. After overnight in the oven, the gel was removed and covered on each side with paper towel pieces cut to approximately the dimensions of the gel and stored in a zip lock plastic bag until used.

EXAMPLE 5

Synthesis of a Gel Containing Formic Acid in Crosslinked Polyacrylic Acid for Laboratory Comparison Methylene-bis-acrylamide (25 mg) was dissolved in 4.0 ml of formic acid (106 mmole). To that solution was added 2.5 ml of acrylic acid (36.5 mmole). Ammonium persulfate (125 mg) was dissolved in 2.5 ml of distilled water. The solutions were combined to achieve a final volume of 9.0 ml. The combined solution was poured into a plastic box. Nitrogen was bubbled through the combined solution, then the box covered tightly and placed into an oven at 50–60° C. overnight to polymerize into a gel. After overnight in the oven, the gel was removed and covered on each side with paper towel pieces cut to approximately the dimensions of the gel and stored in a zip lock plastic bag until used.

EXAMPLE 6

Synthesis of Sodium Formate in AMPS Gel for Laboratory Comparisons

Sodium formate (8.2 gm, 120.6 mmole) and 50 mg of methylenebisacrylamide were dissolved in 15 ml of distilled water. To that solution was added 26 gm (125.4 mmole) of 2-acrylamido-2-methyl-1-propanesulfonic acid (AMPS) and 200 mg of ammonium persulfate. Final volume prior to polymerization was 17.7 ml. Nitrogen was bubbled through the solution, which was then polymerized in an oven at about 55° C. overnight.

EXAMPLE 7

Laboratory Comparison of Release Rates and Durations of Different Gel Formulations For laboratory comparisons of release rates from different formulations, the gels prepared according to Examples 3–6 above were each placed in a plastic box (42×29×15 cm) having covers that were propped open at one end using a piece of glass tubing (0.6 cm in diameter). The formic acid vapor concentrations were measured at periodic intervals by inserting tubing into the box from which vapor was drawn through a solution containing a pH indicator dye in a vial using a hand pump. Formic acid vapors were measured by preparing a solution of 0.1 mg/ml Congo Red (turns from red to blue between pH 5 and 3) and 0.01 mM NaOH in distilled water. Vapors from a box containing the gel to be tested were bubbled through the solution using a Draeger accuro pump (Fisher Scientific). The pump pulls 100 cc of vapor per stroke according to the manufacturer's specifications. The number of strokes required to turn the solution from red to blue provided a relative measure of the formic acid vapor concentration in the box. If the solution did not start to turn color by 20 strokes, the measurement was recorded as 20+ strokes. If, by 20 strokes, the solution had started to turn color, pumping was continued and the actual number of stokes to turn the color from red to blue was recorded. A factor that limited the duration of release of formic acid from gels containing sodium formate was the gels drying out, which is less of an issue in a hive where the bees are producing moisture. In the following table of results, the lowest numbers represent the highest concentrations of formic acid. Results are shown in Table I below:

TABLE I

Comparison of vapor release from various gel formulations.

| Gel | 1 Day | 2 Days | 3 Days | 4 Days | 5 Days | 6 Days |
| --- | --- | --- | --- | --- | --- | --- |
| Example 5 | 2 | 15 | 15 | 16 | 20+ | 20+ |
| Example 3 | 6 | 6 | 4 | 5 | 22 | 20+ |
| Example 4 | 11 | 11 | 8 | 8 | 12 | 21 |
| Example 6 | 4 | 9 | 5 | 6 | 19 | 20+ |

As shown in Table I, release of formic acid vapors from the polymer gel compositions was controlled by varying the composition of the polymer gels. The polymer gel prepared according to the procedure of Example 5 included formic acid in polyacrylic acid. This formulation demonstrated the highest relative concentration of formic acid vapors in the first day, followed by a significant decrease in the concentration by two days (the lowest relative vapor concentration at day 2), and this lower concentration (relative to the other gel formulations) was maintained for the duration of the experiment.

The polymer gel prepared according to Example 3 included formic acid and sodium formate in polyacrylic acid. This formulation demonstrated a relatively slower release rate than Example 5, as the vapor concentration was lower at Day 1, but relatively higher than the formulation of Example 5 at Days 2 through 4.

The polymer gel prepared according to Example 4 included formic acid and sodium formate in poly(acrylic/maleic) acid. The results for this polymer gel show that the addition of maleic anhydride to the polymer matrix slowed release of formic acid vapors relative to the gel formulation prepared according to Example 3. The vapor concentrations for this gel were lower than those of the gel of Example 3 for Days 1–4; however, at Days 5 and 6, the relative concentration was higher than that of Example 3.

The polymer gel prepared according to Example 6 included sodium formate and polyAMPS. This polymer gel showed a relatively slower release rate than the gels prepared in Examples 3 and 4. The vapor concentrations for this gel were relatively higher than those of Examples 3 and 4 until approximately Day 4.

Thus, results illustrate that inclusion of a salt of formic acid (in the present examples, sodium formate) slowed the release of formic acid vapors from the polymeric matrices. Moreover, polymer gel prepared using polyAMPS slowed release of formic acid vapors from the material. These two parameters (inclusion of formic acid salt, selection of monomer for polymer gel preparation, or a combination of the two) can be controlled to control the release of formic acid vapors according to the invention.

Although the concentrations of active agents varied somewhat in the formulations prepared in Examples 3 through 6, this variation did not significantly affect the release rate of the formic acid vapors from the gel compositions. The procedures described in Examples 3 and 6 were repeated, wherein the volumes of active agents were more closely matched, and similar results to those described herein were achieved (data not shown).

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims. All patents, patent documents, and publications cited herein are hereby incorporated by reference as if individually incorporated.

I claim:

1. A controlled release composition for treatment of honeybees, the composition comprising a covalently crosslinked polymer gel and an active agent comprising a salt of formic acid.

2. The controlled release composition according to claim 1 wherein the active agent further comprises formic acid.

3. The controlled release composition according to claim 2 wherein the formic acid is present in an amount in the range of 1% to 70% by weight, based upon the weight of the composition.

4. The controlled release composition according to claim 1 wherein the covalently crosslinked polymer gel is comprised of crosslinked polyacrylic acid or a copolymer of acrylic acid and maleic acid.

5. The controlled release composition according to claim 1 wherein the salt of formic acid is sodium formate.

6. The controlled release composition according to claim 1 wherein the salt of formic acid is present in an amount in the range of 1% to 50% by weight, based upon the weight of the composition.

7. The controlled release composition according to claim 1 further comprising a support material associated with the crosslinked polymer gel.

8. The controlled release composition according to claim 7 wherein the support material comprises a fibrous material.

9. The controlled release composition according to claim 8 wherein the fibrous material comprises nonwoven high-density polyethylene.

10. The controlled release composition according to claim 1 wherein the crosslinked polymer gel includes a crosslinking agent selected from N,N-methylene-bis-acrylamide, N,N-(1,2, dihydroxyethylene) bisacrylamide, 3-(acryloxy)-2-hydroxypropyl methacrylate, ethylene glycol dimethacrylate, ethylene glycol diacrylate, and mixtures thereof.

11. The controlled release composition according to claim 1 wherein the gel further comprises a releasing agent.

12. The controlled release composition according to claim 11 wherein the releasing agent is a nonvolatile acid.

13. The controlled release composition according to claim 12 wherein the nonvolatile acid is selected from malic acid, oxalic acid, citric acid, lactic acid, phosphoric acid, sulfuric acid, and combinations thereof.

14. A method for controlling parasitic mites in honeybees, the method comprising treating the honeybees with a controlled release composition comprising a covalently crosslinked polymer gel and an active agent comprising a salt of formic acid.

15. The method according to claim 14 wherein the active agent further comprises formic acid.

16. The method according to claim 15 wherein the treating comprises delivering the active agent at an effective dose over a period of at least one honeybee brood cycle.

17. The method according to claim 14 wherein the step of treating the honeybees comprises placing the covalently crosslinked polymer gel in proximity to a honeybee hive so that the honeybee hive is exposed to formic acid vapors in a concentration sufficient to control the parasitic mites.

18. The method according to claim 14 wherein the covalently crosslinked polymer gel is comprised of crosslinked polyacrylic acid or a copolymer of acrylic acid and maleic acid.

19. The method according to claim 14 wherein the salt of formic acid is sodium formate.

20. The method according to claim 14 wherein to salt of formic acid is present in an amount in the range of 1% to 50% by weight, based upon the weight of the controlled release composition.

21. The method according to claim 14 wherein the treating comprises delivering the active agent at an effective dose over a period of at least one honeybee brood cycle.

22. The method according to claim 14 wherein the crosslinked polymer gel includes a crosslinking agent selected from N,N-methylene-bis-acrylamide, N,N-(1,2-dihydroxyethylene) bisacrylamide, 3-(acryloxy)-2-hydroxypropyl methacrylate, ethylene glycol dimethacrylate, ethylene glycol diacrylate, and mixtures thereof.

23. A kit for treatment of parasitic mites in honeybees, the kit comprising an envelope containing a controlled release composition comprising a covalently crosslinked polymer gel and an active agent comprising a salt of formic acid, formic acid, or a combination of a salt of formic acid and formic acid.

24. The kit according to claim 23 wherein the envelope is fabricated from a hydrophobic porous material.

25. The kit according to claim 24 wherein the hydrophobic porous material is a nonwoven polyolefin.

26. The kit according to claim 25 wherein the nonwoven polyolefin is a high-density polyethylene material.

27. The kit according to claim 23 further comprising a support material associated with the controlled release composition within the envelope.

28. The kit according to claim 23 further comprising an outer packaging.

29. A controlled release composition for treatment of honeybees for parasitic mites, the composition comprising a covalently crosslinked polymer gel that releases formic acid vapors.

30. The controlled release composition according to claim 29 wherein the covalently crosslinked polymer gel includes an active agent comprising formic acid, a salt of formic acid, or a combination of formic acid and a salt of formic acid.

31. A method for making a non-flowable polymeric gel for controlled release of formic acid vapors, the method comprising polymerizing one or more monomers in the presence of one or more active agents and one or more crosslinking agents to form a covalently crosslinked polymer gel that includes the active agents, wherein the one or more active agents comprise formic acid, a salt of formic acid, or a combination of formic acid and a salt of formic acid.

32. The method according to claim 31 wherein the one or more monomers are selected from acrylic acid, maleic acid, 2-acrylamido-2-methyl-1-propanesulfonic acid, methacrylic acid, maleic anhydride, acrylamide, N,N-dimethylacrylamide, N,N-dimethylacrylic acid, hydroxyethylmethacrylate, hydroxyethylacrylate, and combinations of any of these.

33. The method according to claim 31 wherein the one or more crosslinking agents are selected from N,N-methylene-bis-acrylamide, N,N'-(1,2-dihydroxyethylene)bisacrylamide, 3-(acryloyloxy)-2-hydroxypropyl methacrylate, ethylene glycol dimethacrylate, ethylene glycol diacrylate, and combinations of any of these.

* * * * *